(12) United States Patent
Nevala et al.

(10) Patent No.: US 11,531,030 B2
(45) Date of Patent: Dec. 20, 2022

(54) POLYPEPTIDE-ANTIBODY COMPLEXES AND USES THEREOF

(71) Applicant: Mayo Foundation for Medical Education and Research, Rochester, MN (US)

(72) Inventors: Wendy K. Nevala, Rochester, MN (US); Svetomir N. Markovic, Rochester, MN (US); John T. Butterfield, Edina, MN (US); Daniel J. Knauer, Costa Mesa, CA (US)

(73) Assignee: MAYO FOUNDATION FOR MEDICAL EDUCATION AND RESEARCH, Rochester, MN (US)

(*) Notice: Subject to any disclaimer, the term of this patent is extended or adjusted under 35 U.S.C. 154(b) by 409 days.

(21) Appl. No.: 16/603,466

(22) PCT Filed: Apr. 20, 2018

(86) PCT No.: PCT/US2018/028557
§ 371 (c)(1),
(2) Date: Oct. 7, 2019

(87) PCT Pub. No.: WO2018/195416
PCT Pub. Date: Oct. 25, 2018

(65) Prior Publication Data
US 2021/0132068 A1 May 6, 2021

Related U.S. Application Data

(60) Provisional application No. 62/626,790, filed on Feb. 6, 2018, provisional application No. 62/488,392, filed on Apr. 21, 2017.

(51) Int. Cl.
| | | |
|---|---|---|
| *G01N 33/574* | (2006.01) | |
| *C07K 14/00* | (2006.01) | |
| *C07K 16/28* | (2006.01) | |
| *C07K 16/32* | (2006.01) | |

(52) U.S. Cl.
CPC ....... *G01N 33/5748* (2013.01); *C07K 14/001* (2013.01); *C07K 16/2827* (2013.01); *C07K 16/2887* (2013.01); *C07K 16/32* (2013.01); *G01N 33/57492* (2013.01)

(58) Field of Classification Search
CPC ......... G01N 33/5748; G01N 33/57492; C07K 14/001; C07K 16/2827; C07K 16/2887; C07K 16/32; C07K 2317/24; C07K 19/00; C07K 14/765
See application file for complete search history.

(56) References Cited

U.S. PATENT DOCUMENTS

| | | | |
|---|---|---|---|
| 9,427,477 B2 | 8/2016 | Markovic et al. | |
| 9,446,148 B2 | 9/2016 | Markovic et al. | |
| 9,533,058 B2 | 1/2017 | Markovic et al. | |
| 9,555,128 B2 | 1/2017 | Markovic et al. | |
| 9,566,350 B2 | 2/2017 | Markovic et al. | |
| 9,757,453 B2 | 9/2017 | Markovic et al. | |
| 10,213,513 B2 | 2/2019 | Markovic et al. | |
| 10,279,035 B2 | 5/2019 | Markovic et al. | |
| 10,279,036 B2 | 5/2019 | Markovic et al. | |
| 10,300,016 B2 | 5/2019 | Markovic et al. | |
| 10,307,482 B2 | 6/2019 | Markovic et al. | |
| 10,322,084 B2 | 6/2019 | Markovic et al. | |
| 10,376,579 B2 | 8/2019 | Markovic et al. | |
| 10,376,580 B2 | 8/2019 | Markovic et al. | |
| 10,391,055 B2 | 8/2019 | Markovic et al. | |
| 10,406,224 B2 | 9/2019 | Markovic et al. | |
| 10,413,606 B2 | 9/2019 | Markovic et al. | |
| 10,420,839 B2 | 9/2019 | Markovic et al. | |
| 10,441,656 B2 | 10/2019 | Markovic et al. | |
| 10,471,145 B2 | 11/2019 | Markovic et al. | |
| 10,478,495 B2 | 11/2019 | Markovic et al. | |
| 10,493,150 B2 | 12/2019 | Markovic et al. | |
| 10,507,243 B2 | 12/2019 | Markovic et al. | |
| 10,561,726 B2 | 2/2020 | Markovic et al. | |
| 10,596,111 B2 | 3/2020 | Markovic et al. | |
| 10,596,112 B2 | 3/2020 | Markovic et al. | |
| 10,610,484 B2 | 4/2020 | Markovic et al. | |
| 10,618,969 B2 | 4/2020 | Markovic et al. | |
| 10,624,846 B2 | 4/2020 | Markovic et al. | |
| 10,668,151 B2 | 6/2020 | Markovic et al. | |
| 2009/0263483 A1 | 10/2009 | Desai et al. | |
| 2010/0035284 A1 | 2/2010 | Buhimschi et al. | |
| 2014/0066378 A1 | 3/2014 | Dixit et al. | |
| 2014/0080901 A1 | 3/2014 | Desai et al. | |
| 2015/0246122 A1 | 9/2015 | Markovic et al. | |
| 2016/0207979 A1 | 7/2016 | Dixit et al. | |
| 2016/0250351 A1 | 9/2016 | Markovic et al. | |
| 2016/0339118 A1 | 11/2016 | Markovic et al. | |
| 2017/0021034 A1 | 1/2017 | Markovic et al. | |
| 2017/0071897 A1 | 3/2017 | Markovic et al. | |
| 2017/0106087 A1 | 4/2017 | Markovic et al. | |
| 2017/0182175 A1 | 6/2017 | Markovic et al. | |
| 2017/0182180 A1 | 6/2017 | Markovic et al. | |
| 2017/0182183 A1 | 6/2017 | Markovic et al. | |
| 2017/0182187 A1 | 6/2017 | Markovic et al. | |
| 2017/0216453 A1 | 8/2017 | Markovic et al. | |
| 2017/0232102 A1 | 8/2017 | Markovic et al. | |
| 2018/0235886 A1 | 8/2018 | Markovic et al. | |

(Continued)

FOREIGN PATENT DOCUMENTS

| | | |
|---|---|---|
| WO | WO 2016/131962 | 8/2016 |
| WO | WO 2018/027205 | 2/2018 |
| WO | WO 2018/195416 | 10/2018 |

OTHER PUBLICATIONS

Allen, "Ligand-targeted therapeutics in anticancer therapy," Nature Reviews Cancer, 2(10):750-63, Oct. 2002.

(Continued)

*Primary Examiner* — Kimberly Ballard
*Assistant Examiner* — Stacey N MacFarlane
(74) *Attorney, Agent, or Firm* — Baker Botts L.L.P.

(57) ABSTRACT

Complexes containing a labeled polypeptide and an antibody, and the use of such complexes as research, diagnostic, and clinical tools, are described herein.

17 Claims, 7 Drawing Sheets

Specification includes a Sequence Listing.

(56) References Cited

U.S. PATENT DOCUMENTS

| | | |
|---|---|---|
| 2019/0038761 A1 | 2/2019 | Markovic et al. |
| 2019/0099498 A1 | 4/2019 | Markovic et al. |
| 2019/0184032 A1 | 6/2019 | Markovic et al. |
| 2019/0201546 A1 | 7/2019 | Markovic et al. |
| 2019/0202916 A1 | 7/2019 | Markovic et al. |
| 2019/0216944 A1 | 7/2019 | Markovic et al. |

OTHER PUBLICATIONS

Carugo and Pongor, "A normalized root-mean-square distance for comparing protein three-dimensional structures," Protein Science, 10(7):1470-3, Jul. 2001.

Carvalho et al., "Immunotherapy of cancer: from monoclonal to oligoclonal cocktails of anti-cancer antibodies: IUPHAR Review 18," British Journal of Pharmacology, 173(9):1407-24, May 2016.

Cho et al., "Structure of the extracellular region of HER2 alone and in complex with the Herceptin Fab," Nature, 421(6924):756-60, Feb. 2003.

Desai, "Nanoparticle albumin bound (nab) technology : A nanotechnology platform for biologically interactive drug delivery and targeting," FDA Document TS15, The 234th ACS National Meeting, Boston, MA, Aug. 19-23, 2007.

Diamantis and Banerji, "Antibody-drug conjugates—an emerging class of cancer treatment," British Journal of Cancer, 114(4):362-7, Feb. 2016.

Du et al., "Structural basis for recognition of CD20 by therapeutic antibody Rituximab," Journal of Biological Chemistry, 282(20):15073-80, May 2007.

Gelderblom et al., "Cremophor EL: the drawbacks and advantages of vehicle selection for drug formulation," European Journal of Cancer, 37(13):1590-8, Sep. 2001.

Guatelli et al., "Isothermal, in vitro amplification of nucleic acids by a multienzyme reaction modeled after retroviral replication," Proceedings of the National Academy of Sciences, 87(5):1874-8, Mar. 1990.

Harding et al., "The immunogenicity of humanized and fully human antibodies: residual immunogenicity resides in the CDR regions," mAbs, 2(3):256-65, 2010.

Hughes, "Antibody-drug conjugates for cancer: poised to deliver?" Nature Reviews Drug Discovery, 9(9):665-667, 2010.

International Preliminary Report on Patentability International Application No. PCT/US2018/028557 dated Oct. 22, 2019, 10 pages.

International Search Report & Written Opinion in International Application No. PCT/US2018/028557 dated Sep. 7, 2018, 20 pages.

Kratz, "Albumin as a drug carrier: Design of prodrugs, drug conjugates and nanoparticles," Journal of Controlled Release, 132(3):171-183, 2008.

Krissinel et al., "Secondary structure matching (SSM), a new tool for fast protein structure alignment in three dimensions," Acta Crystallographica Section D Biological Crystallography, 60(12), 2256-2268, 2004.

Laurenzi et al., "Structure prediction of partial-length protein sequences," International Journal of Molecular Sciences, 14(7):14892-907, 2013.

Lee et al., "Peptide-based probes for targeted molecular imaging," Biochemistry, 49(7):1364-76, 2010.

Lewis, "PCR's Competitors are Alive and Well and Moving Rapidly Towards Commercialization," Genetic Engineering News, 12(9):1-3, 1992.

Lim et al., "Anti-CD20 monoclonal antibodies: historical and future perspectives," Haematologica, 95(1):135-43, Jan. 2010.

Molina et al., "Trastuzumab (herceptin), a humanized anti-Her2 receptor monoclonal antibody, inhibits basal and activated Her2 ectodomain cleavage in breast cancer cells," Cancer Research, 61(12):4744-9, Jun. 2001.

Muller et al., "VEGF and the Fab fragment of a humanized neutralizing antibody: crystal structure of the complex at 2.4 å resolution and mutational analysis of the interface," Structure, 6(9):1153-1167, 1998.

Nevala et al., "Antibody-Targeted Chemotherapy for the Treatment of Melanoma," Cancer Research, 76(13), 2016.

Panowski et al., "Site-specific antibody drug conjugates for cancer therapy," mAbs, 6(1):34-45, 2014.

Petsalaki et al., "Accurate Prediction of Peptide Binding Sites on Protein Surfaces," PLoS Computational Biology, 5(3):e1000335, Mar. 2009.

Pettersen et al., "UCSF Chimera—a visualization system for exploratory research and analysis," Journal of Computational Chemistry, 25(13):1605-1612, Oct. 2004.

Roy et al., "Molecular and structural basis of drift in the functions of closely-related homologous enzyme domains: implications for function annotation based on homology searches and structural genomics," In Silico Biology, 9(1-2):S41-55, 2009.

Schrama et al., "Antibody targeted drugs as cancer therapeutics," Nature Reviews Drug Discovery, 5(2):147-59, Feb. 2006.

Shen et al., "Improved PEP-FOLD Approach for Peptide and Miniprotein Structure Prediction," Journal of Chemical Theory and Computation, 10(10):4745-4758, 2014.

Sudlow et al., "Further characterization of specific drug binding sites on human serum albumin," Molecular Pharmacology, 12(6):1052-1061, Nov. 1976.

Sugio et al., "Crystal structure of human serum albumin at 2.5 A resolution," Protein Engineering, 12(6):439-46, Jun. 1999.

Tanaka et al., "Modification of the single unpaired sulfhydryl group of β-lactoglobulin under high pressure and the role of intermolecular S-S exchange in the pressure denaturation [Single SH of β-lactoglobulin and pressure denaturation]," International Journal of Biological Macromolecules, 19(1):63-68, Jul. 1996.

Tanaka et al., "Structure of pressure-induced denatured state of human serum albumin: a comparison with the intermediate in urea-induced denaturation," Biochimica et Biophysica Acta (BBA)—Protein Structure and Molecular Enzymology, 1338(1):13-20, Mar. 1997.

Thévenet et al., "PEP-FOLD: an updated de novo structure prediction server for both linear and disulfide bonded cyclic peptides," Nucleic Acids Research, 40(Web Server issue):W288-93, 2012.

Weiss, "Hot prospect for new gene amplifier," Science, 254(5036):1292-4, Nov. 1991.

Yu et al., "Interaction between bevacizumab and murine VEGF-A: a reassessment," Investigative Ophthalmology & Visual Science, 49(2):522-7, Feb. 2008.

U.S. Appl. No. 16/967,229, filed Aug. 4, 2020, Wendy K. Nevala, Pending.

Chen et al., "Selection and analysis of an optimized anti-VEGF antibody: crystal structure of an affinity-matured fab in complex with antigen," J. Mol. Biology, 293(4):865-881.

Collaborative Computational Project, No. 4, "The CCP4 Suite: Programs for Protein Crystallography," Acta Crystallography, 50(Pt 5):760-763, Sep. 1994.

Papadopoulos et al., "Binding and neutralization of vascular endothelial growth factor (VEGF) and related ligands by VEGF Trap, ranibizumab and bevacizumab," Angiogenesis, 15(2):171-185, Feb. 2012.

SEQUENCE LISTING

```
<160> NUMBER OF SEQ ID NOS: 10

<210> SEQ ID NO 1
<211> LENGTH: 18
<212> TYPE: PRT
<213> ORGANISM: Homo sapiens

<400> SEQUENCE: 1

Val Val Leu Asn Gln Leu Cys Val Leu His Glu Lys Thr Pro Val Ser
1               5                   10                  15

Asp Arg

<210> SEQ ID NO 2
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 2

Cys Gly Ser Gly Gly Gly Ser
1               5

<210> SEQ ID NO 3
<211> LENGTH: 25
<212> TYPE: PRT
<213> ORGANISM: Artificial Sequence
```

```
<220> FEATURE:
<223> OTHER INFORMATION: synthetic polypeptide

<400> SEQUENCE: 3

Cys Gly Ser Gly Gly Gly Ser Val Val Leu Asn Gln Leu Cys Val Leu
1               5                   10                  15

His Glu Lys Thr Pro Val Ser Asp Arg
            20                  25

<210> SEQ ID NO 4
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 4

Ser Gly Gly Gly Ser Gly Cys
1               5

<210> SEQ ID NO 5
<211> LENGTH: 25
<212> TYPE: PRT
<213> ORGANISM: Artificial Sequence
<220> FEATURE:
<223> OTHER INFORMATION: synthetic polypeptide

<400> SEQUENCE: 5

Val Val Leu Asn Gln Leu Cys Val Leu His Glu Lys Thr Pro Val Ser
1               5                   10                  15

Asp Arg Gly Ser Gly Gly Gly Ser Cys
            20                  25

<210> SEQ ID NO 6
<211> LENGTH: 25
<212> TYPE: PRT
<213> ORGANISM: Artificial Sequence
<220> FEATURE:
<223> OTHER INFORMATION: synthetic polypeptide

<400> SEQUENCE: 6

Val Val Leu Asn Gln Leu Cys Val Leu His Glu Lys Thr Pro Val Ser
1               5                   10                  15

Asp Arg Ser Gly Gly Gly Ser Gly Cys
            20                  25

<210> SEQ ID NO 7
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 7

Lys Ser Ser Ser Asp
1               5

<210> SEQ ID NO 8
<211> LENGTH: 5
<212> TYPE: PRT
<213> ORGANISM: Artificial Sequence
<220> FEATURE:
<223> OTHER INFORMATION: synthetic polypeptide
```

```
<400> SEQUENCE: 8

Lys Ser Ser Ser Asp
1               5

<210> SEQ ID NO 9
<211> LENGTH: 23
<212> TYPE: PRT
<213> ORGANISM: Artificial Sequence
<220> FEATURE:
<223> OTHER INFORMATION: synthetic polypeptide

<400> SEQUENCE: 9

Lys Ser Ser Asp Val Val Leu Asn Gln Leu Cys Val Leu His Glu
1               5                   10                  15

Lys Thr Pro Val Ser Asp Arg
            20

<210> SEQ ID NO 10
<211> LENGTH: 23
<212> TYPE: PRT
<213> ORGANISM: Artificial Sequence
<220> FEATURE:
<223> OTHER INFORMATION: synthetic polypeptide

<400> SEQUENCE: 10

Val Val Leu Asn Gln Leu Cys Val Leu His Glu Lys Thr Pro Val Ser
1               5                   10                  15

Asp Arg Asp Ser Ser Ser Lys
            20
```

POLYPEPTIDE-ANTIBODY COMPLEXES AND USES THEREOF

CROSS-REFERENCE TO RELATED APPLICATIONS

This application is a National Stage application under 35 U.S.C. § 371 of International Application No. PCT/US2018/028557, having an International Filing Date of Apr. 20, 2018, which claims benefit of priority from U.S. Provisional Application Ser. No. 62/626,790, filed on Feb. 6, 2018, and U.S. Provisional Application Ser. No. 62/488,392, filed on Apr. 21, 2017, all of which are incorporated herein by reference in their entirety.

TECHNICAL FIELD

This document relates to methods and materials that can be used to, for example, image cells (e.g., cancer cells) in vitro or within mammals (e.g., humans). For example, this document provides polypeptide complexes that include (a) a polypeptide component, (b) an antibody, and (c) a label. Such polypeptide complexes can be used as research and clinical tools.

BACKGROUND

Many different antibody therapeutics have been developed to treat diseases. For example, monoclonal antibodies such as bevacizumab, rituximab, and trastuzumab were developed to treat cancer. Typically, therapeutic antibodies are used to inhibit the activity of a targeted polypeptide within a mammal being treated, or are used to deliver other agents (e.g., toxic drugs) to cells expressing the targeted polypeptide.

SUMMARY

This document is based, at least in part, on the development of methods and materials for imaging cells (e.g., cancer cells) in vitro or within mammals (e.g., humans). For example, this document provides polypeptide complexes that include (a) a polypeptide component, (b) an antibody, and (c) a label (e.g., a label conjugated to the polypeptide component). Such polypeptide complexes can be used as research and clinical tools, and may provide advantages over directly labeled antibodies.

As described herein, a polypeptide-antibody complex can include a polypeptide component that contains the amino acid sequence of SEQ ID NO:1 (VVLNQLCVLHEKTPVSDR) preceded by an N-terminal amino acid sequence (e.g., CGSGGGS; SEQ ID NO:2) that may be labeled. An example of such a polypeptide component is CGSGGGSVVLNQLCVLHEKTPVSDR (SEQ ID NO:3). In some cases, a polypeptide-antibody complex provided herein can include a polypeptide component that includes the amino acid sequence of SEQ ID NO:1 followed by a C-terminal amino acid sequence (e.g., SGGGSGC; SEQ ID NO:4) that may be labeled. Examples of such a polypeptide component include VVLNQLCVLHEKTPVS-DRGSGGGSC (SEQ ID NO:5) and VVLNQLCVLHEK-TPVSDRSGGGSGC (SEQ ID NO:6). The polypeptide component can be labeled with, e.g., a radionuclide or a fluorescent particle (e.g., a Quantum Dot; "QD").

In some embodiments, a polypeptide-antibody complex can include a polypeptide component that contains the amino acid sequence of SEQ ID NO:1 (VVLNQLCVLHEK TPVSDR) preceded by an N-terminal amino acid sequence or followed by a C-terminal amino acid sequence that is five to seven (e.g., five to six, six to seven, five, six, or seven) amino acids in length and includes a terminal lysine residue that can be coupled to biotin and labeled. For example, a polypeptide can include the sequence KSSSD (SEQ ID NO:7) at its N-terminus, or the sequence DSSSK (SEQ ID NO:8) at its C-terminus. Examples of such polypeptide components thus include KSSSDVVLNQLCVLHEKT PVSDR (SEQ ID NO:9) and VVLNQLCVLHEKTPVS-DRDSSSK (SEQ ID NO:10). The polypeptide component can be labeled with, e.g., a streptavidin-coupled QD via a biotin-streptavidin linkage.

The polypeptide component can non-covalently bind to the variable regions of multiple different therapeutic monoclonal antibodies including, without limitation, bevacizumab, rituximab, trastuzumab, alemtuzumab, atezolizumab, blinatumomab, brentuximab, cetuximab, denosumab, dinutuximab, ibritumomab, ipilimumab, nivolumab, obinutuzumab, ofatumumab, panitumumab, pembrolizumab, pertumumab, gemtuzumab, tositumomab, muromonab, and biosimilars thereof. To form a polypeptide-antibody complex as described herein, one or more antibodies (e.g., therapeutic antibodies) can be non-covalently attached to a polypeptide component provided herein. Such polypeptide-antibody complexes can be used in vitro or in vivo to visualize cells or tissues expressing antigens targeted by the antibody of the complex. For example, a polypeptide-antibody complex provided herein can be used to image cells or tissue (e.g., tumor tissue) using clinical tests such as computerized tomography (CT) or positron emission tomography (PET) scans. This flexible tool may be employed to ascertain patient tumor burden in most, if not all, cancer types that have tumor-specific protein expression. Such uses of the polypeptide-antibody complexes provided herein can be advantageous, as the return of emission can be very strong given the semi-conductor nature of labels such as Quantum Dots (QDs). In addition, emission can occur in three directions, without following the usual $1/r^2$ rule of signal disintegration.

In one aspect, this document features an isolated polypeptide containing the amino acid sequence set forth in SEQ ID NO:3, or a sequence that is at least 92% identical to SEQ ID NO:3. The polypeptide can include the amino acid sequence set forth in SEQ ID NO:3, but with one or two amino acid deletions, additions, or substitutions within the N-terminal seven amino acids of SEQ ID NO:3. The polypeptide can be labeled. The label can be a fluorescent moiety (e.g., fluorescein, sulforhodamine B, tetramethylrhodamine, phycoerithrin, Quantum Dots, or allophycocyanin). The label can be a radionuclide (e.g., $^3$H, $^{13}$C, $^{15}$N, $^{125}$I, or $^{99}$Tcm).

In another aspect, this document features an isolated polypeptide, where the amino acid sequence of the polypeptide consists of the sequence set forth in SEQ ID NO:3. The polypeptide can be labeled. The label can be fluorescent moiety (e.g., fluorescein, sulforhodamine B, tetramethylrhodamine, phycoerithrin, Quantum Dots, or allophycocyanin). The label can be a radionuclide (e.g., $^3$H, $^{13}$C, $^{15}$N, $^{125}$I, or $^{99}$Tcm).

In another aspect, this document features a complex containing (a) a polypeptide that contains the amino acid sequence set forth in SEQ ID NO:3, or a sequence that is at least 92% identical to SEQ ID NO:3, and (b) an antibody. The polypeptide can include the amino acid sequence of SEQ ID NO:3, but with one or two amino acid deletions, additions, or substitutions within the N-terminal seven amino acids of SEQ ID NO:3. The polypeptide can be labeled. The label can be fluorescent moiety (e.g., fluorescein, sulforhodamine B, tetramethylrhodamine, phycoerithrin, Quantum Dots, or allophycocyanin). The label can be a radionuclide (e.g., $^3$H, $^{13}$C, $^{15}$N, $^{125}$I, or $^{99}$Tcm). The antibody can bind specifically to a tumor or $^{99}$Tcm). The antibody can bind specifically to a tumor antigen. The tumor antigen can be vascular endothelial growth factor (VEGF), programmed death-ligand 1 (PD-L1), HER2, or CD20.

In still another aspect, this document features a complex containing (a) a purified polypeptide, where the amino acid sequence of the polypeptide consists of the sequence set forth in SEQ ID NO:3, and (b) an antibody. The polypeptide can be labeled. The label can be fluorescent moiety (e.g., fluorescein, sulforhodamine B, tetramethylrhodamine, phycoerithrin, Quantum Dots, or allophycocyanin). The label can be a radionuclide (e.g., $^3$H, $^{13}$C, $^{15}$N, $^{125}$I, or $^{99}$Tcm). The antibody can bind specifically to a tumor antigen (e.g., VEGF, PD-L1, HER2, or CD20).

This document also features a method for detecting a cell expressing on its surface a selected antigen, where the method includes contacting the cell with a complex that includes (a) a detectably labeled polypeptide containing the sequence set forth in SEQ ID NO:3, or containing a sequence that is at least 92% identical to the sequence set forth in SEQ ID NO:3, and (b) an antibody that binds selectively to the antigen, where the contacting is under conditions in which the antibody can bind to the antigen, and detecting the presence of the label on the cell. The polypeptide can contain the amino acid sequence of SEQ ID NO:3, but with one or two amino acid deletions, additions, or substitutions within the N-terminal seven amino acids of SEQ ID NO:3. The polypeptide can be labeled with be fluorescent moiety (e.g., fluorescein, sulforhodamine B, tetramethylrhodamine, phycoerithrin, Quantum Dots, or allophycocyanin). The polypeptide can be labeled with a radionuclide (e.g., $^3$H, $^{13}$C, $^{15}$N, $^{125}$I, or $^{99}$Tcm). The method can further include removing unbound complex from the cell.

In another aspect, this document features an isolated polypeptide containing the amino acid sequence set forth in SEQ ID NO:10, or a sequence that is at least 91% identical to SEQ ID NO:10. The polypeptide can include the amino acid sequence set forth in SEQ ID NO:10, but with one or two amino acid deletions, additions, or substitutions within the C-terminal five amino acids of SEQ ID NO:10. The polypeptide can be coupled to biotin. The polypeptide can be labeled. In some cases, the polypeptide can be coupled to biotin and labeled with a label coupled to streptavidin. The label can be a fluorescent moiety (e.g., fluorescein, sulforhodamine B, tetramethylrhodamine, phycoerithrin, Quantum Dots, or allophycocyanin). The label can be a radionuclide (e.g., $^3$H, $^{13}$C, $^{15}$N, $^{125}$I, or $^{99}$Tcm).

In another aspect, this document features an isolated polypeptide, where the amino acid sequence of the polypeptide consists of the sequence set forth in SEQ ID NO:10. The polypeptide can be coupled to biotin. The polypeptide can be labeled. In some cases, the polypeptide can be coupled to biotin and labeled with a label coupled to streptavidin. The label can be fluorescent moiety (e.g., fluorescein, sulforhodamine B, tetramethylrhodamine, phycoerithrin, Quantum Dots, or allophycocyanin). The label can be a radionuclide (e.g., $^3$H, $^{13}$C, $^{15}$N, $^{125}$I, or $^{99}$Tcm).

In another aspect, this document features a complex containing (a) a polypeptide that contains the amino acid sequence set forth in SEQ ID NO:10, or a sequence that is at least 91% identical to SEQ ID NO:10, and (b) an antibody. The polypeptide can include the amino acid sequence of SEQ ID NO:10, but with one or two amino acid deletions, additions, or substitutions within the C-terminal five amino acids of SEQ ID NO:10. The polypeptide can be coupled to biotin. The polypeptide can be labeled. In some cases, the polypeptide can be coupled to biotin and labeled with a label coupled to streptavidin. The label can be fluorescent moiety (e.g., fluorescein, sulforhodamine B, tetramethylrhodamine, phycoerithrin, Quantum Dots, or allophycocyanin). The label can be a radionuclide (e.g., $^3$H, $^{13}$C, $^{15}$N, $^{125}$I, or $^{99}$Tcm). The antibody can bind specifically to a tumor antigen. The tumor antigen can be vascular endothelial growth factor (VEGF), programmed death-ligand 1 (PD-L1), HER2, or CD20.

In still another aspect, this document features a complex containing (a) a purified polypeptide, where the amino acid sequence of the polypeptide consists of the sequence set forth in SEQ ID NO:10, and (b) an antibody. The polypeptide can be coupled to biotin. The polypeptide can be labeled. In some cases, the polypeptide can be coupled to biotin and labeled with a label coupled to streptavidin. The label can be fluorescent moiety (e.g., fluorescein, sulforhodamine B, tetramethylrhodamine, phycoerithrin, Quantum Dots, or allophycocyanin). The label can be a radionuclide (e.g., $^3$H, $^{13}$C, $^{15}$N, $^{125}$I, or $^{99}$Tcm). The antibody can bind specifically to a tumor antigen (e.g., VEGF, PD-L1, HER2, or CD20).

This document also features a method for detecting a cell expressing on its surface a selected antigen, where the method includes contacting the cell with a complex that includes (a) a detectably labeled polypeptide containing the sequence set forth in SEQ ID NO:10, or containing a sequence that is at least 91% identical to the sequence set forth in SEQ ID NO:10, and (b) an antibody that binds selectively to the antigen, where the contacting is under conditions in which the antibody can bind to the antigen, and detecting the presence of the label on the cell. The polypeptide can contain the amino acid sequence of SEQ ID NO:10, but with one or two amino acid deletions, additions, or substitutions within the C-terminal five amino acids of SEQ ID NO:10. The polypeptide can be labeled with be fluorescent moiety (e.g., fluorescein, sulforhodamine B, tetramethylrhodamine, phycoerithrin, Quantum Dots, or allophycocyanin). The polypeptide can be labeled with a radionuclide (e.g., $^3$H, $^{13}$C, $^{15}$N, $^{125}$I, or $^{99}$Tcm). In some cases, the polypeptide can be linked to a label via a biotin-streptavidin coupling. The method can further include removing unbound complex from the cell.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 5 also includes histogram plotting the data.

DETAILED DESCRIPTION

Figure 1:
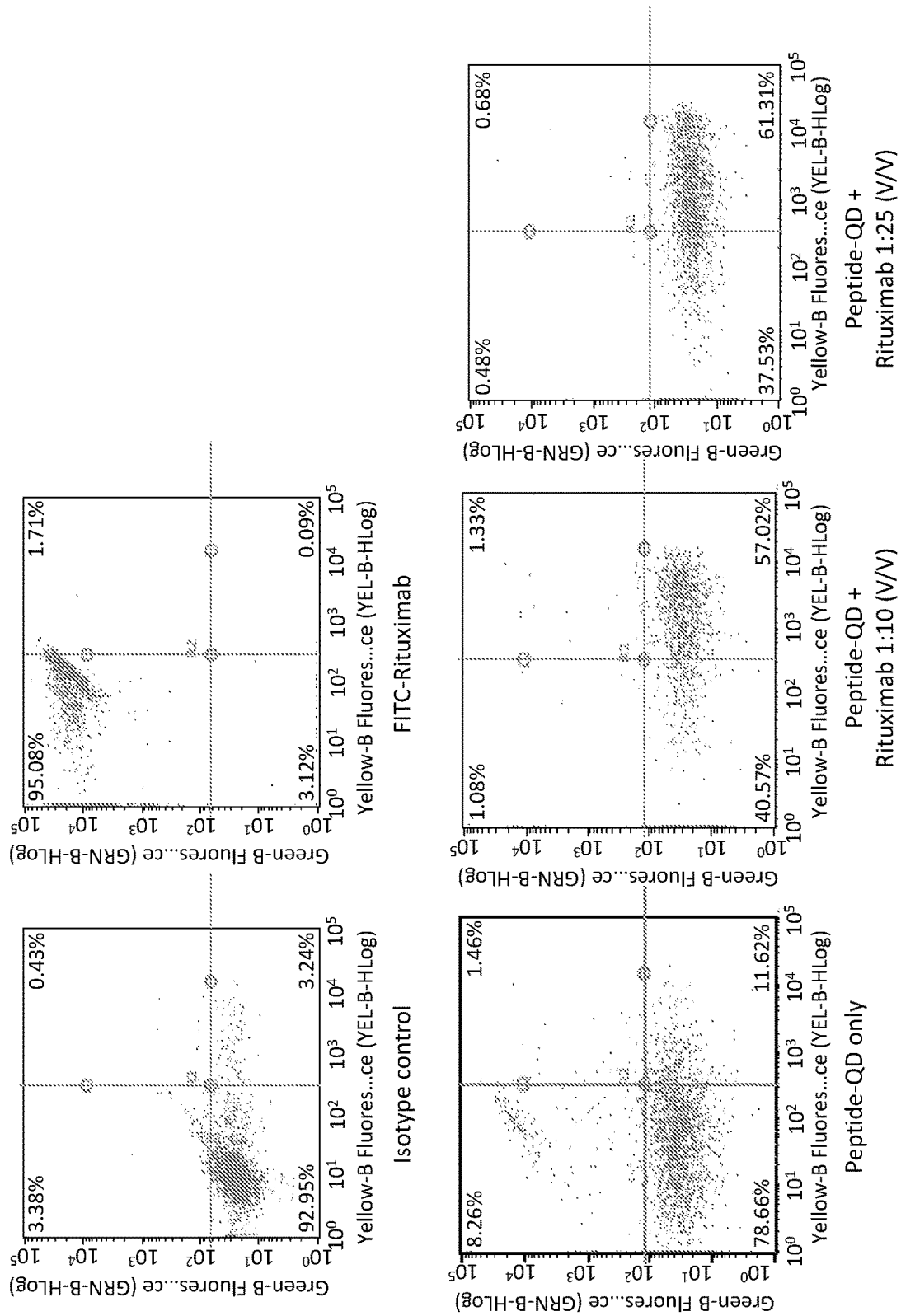
FIG. 1 is a series of scatter plots from flow cytometry studies using a polypeptide having the sequence CGSGGGSVVLNQLCVLHEKTPVSDR (SEQ ID NO:3) that was labeled with QDs that emit at a wavelength of 565 nm, and complexed with a therapeutic antibody (rituximab). The polypeptide-antibody complex was formed by incubating the polypeptide component with rituximab at ratios of 25:1 and 10:1 V/V (50 µl peptide+2 µl rituximab) for 1 hour, resulting in a complex that was stable until at least the next day. CD20+ Daudi lymphoma cells were incubated with isotype control, FITC-rituximab, peptide-QD only, peptide-QD+ rituximab (10:1), and peptide-QD+ rituximab (25:1) for 30 minutes at 4° C. After washing with FACS buffer (PBS+0.5% BSA and 0.5% Na azide), the stained cells were analyzed by flow cytometry for recognition of CD20. The Daudi cells were 95% CD20+ (top left), 11.62% positive when stained with peptide-QD only (bottom left), and 57.02% and 61.31% positive with peptide-QD-rituximab at 10:1 and 25:1 (bottom center and bottom right, respectively).

As described herein, a labeled (e.g., fluorescently tagged) polypeptide component containing SEQ ID NO:1 can have the ability to bind to antibodies (e.g., tumor specific antibodies such as bevacizumab, rituximab, trastuzumab, alemtuzumab, atezolizumab, blinatumomab, brentuximab, cetuximab, denosumab, dinutuximab, ibritumomab, ipilimumab, nivolumab, obinutuzumab, ofatumumab, panitumumab, pembrolizumab, pertumumab, gemtuzumab, tositumomab, and muromonab), forming a complex that in turn can bind to the cell membrane-bound ligand for the antibody, thereby staining the cells positively for the membrane-bound target as determined by flow cytometry or other detection methods. This can provide a diagnostic tool consisting of a single reagent that, when labeled (e.g., fluorescently or radioactively), can be used as a tool to determine tumor burden. For example, a polypeptide component provided herein can be labeled and noncovalently bound to a tumor specific-antibody, which then can be used in standard clinical testing such as PET scanning, CT scanning, and/or fluorescent imaging to evaluate patient tumor burden in cancers that have tumor-specific protein expression (e.g., breast cancer, melanoma, lymphoma, renal cell carcinoma, ovarian cancer, lung cancer, and head and neck cancer). The tagged polypeptide also can provide a research tool that can be used in the development of cancer therapies, for example.

Thus, this document provides purified polypeptides having the sequence CGSGGGSVVLNQLCVLHEKTPVSDR (SEQ ID NO:3), VVLNQLCVLHEKTPVSDR GSGGGSC (SEQ ID NO:5), VVLNQLCVLHEKTPVSDRSGGGSGC (SEQ ID NO:6), KSSSDVVLNQLCVLHEKTPVSDR (SEQ ID NO:9), and/or VLNQLCVLHEKTPVS DRDSSSK (SEQ ID NO:10), and variants thereof, that can bind to multiple therapeutic monoclonal antibodies. The peptides can be labeled with, for example, a radionuclide (e.g., $^{3}H$, $^{13}C$, $^{15}N$, $^{125}I$, or $^{99}Tcm$) or a fluorescent moiety (e.g., fluorescein, sulforhodamine B, tetramethylrhodamine, phycoerithrin, QD, or allophycocyanin), bound to various tumor marker-specific antibodies (e.g., bevacizumab, rituximab, trastuzumab, atezolizumab, or cetuximab), and used as research or diagnostic tools. As described herein, each polypeptide can include an 18 amino acid sequence derived from human serum albumin (HSA) (VVLNQLCVLHEKTPVSDR; SEQ ID NO:1) with an N-terminal tag [e.g., CGSGGGS (SEQ ID NO:2) or KSSSD (SEQ ID NO:7)] that can allow for amino-terminal binding of the polypeptide to a labeling moiety, without inhibiting binding of the polypeptide to a tumor-specific clinical antibody. In some cases, the tag can be at the C-terminus of SEQ ID NO:1, rather than at the N-terminus. Moreover, in some embodiments, the polypeptide can include one or more variations within the SEQ ID NO:1 portion or within the tag sequence at the N- or C-terminus.

The term "isolated," as used herein with reference to a polypeptide, means that the polypeptide (1) is not associated with proteins found in nature, (2) is free of other proteins from the same source (e.g., free of human proteins), (3) is expressed by a cell from a different species, or (4) does not occur in nature. An isolated polypeptide can be, for example, encoded by DNA or RNA, including synthetic DNA or RNA, or some combination thereof.

The term "substantially pure," with reference to a polypeptide, means that the polypeptide is substantially free of other polypeptides, lipids, carbohydrates, and nucleic acid with which it is naturally associated. A substantially pure polypeptide can be any polypeptide that is removed from its natural environment and is at least 60 percent pure. A substantially pure polypeptide can be at least about 65, 70, 75, 80, 85, 90, 95, or 99 percent pure, or about 65 to 75, 75 to 80, 80 to 85, 85 to 90, 90 to 95, or 95 to 99 percent pure. Typically, a substantially pure polypeptide will yield a single major band on a non-reducing polyacrylamide gel. In some embodiments, a substantially pure polypeptide can be a chemically synthesized polypeptide.

Any method can be used to obtain a substantially pure polypeptide. For example, polypeptide purification techniques, such as affinity chromatography and HPLC, as well as polypeptide synthesis techniques can be used. In addition, any material can be used as a source to obtain a substantially pure polypeptide. For example, tissue from wild-type or transgenic animals can be used as a source material. In addition, tissue culture cells engineered to over-express a particular polypeptide can be used to obtain a substantially pure polypeptide. Further, a polypeptide can be engineered to contain an amino acid sequence that allows the polypeptide to be captured onto an affinity matrix. For example, a tag such as c-myc, hemagglutinin, polyhistidine, or FLAG™ tag (Kodak) can be used to aid in polypeptide purification. Such tags can be inserted anywhere within the polypeptide, including at either the carboxyl terminus or the amino terminus, or in between. Other fusions that can be used include enzymes that aid in the detection of the polypeptide, such as alkaline phosphatase.

In some embodiments, a polypeptide as provided herein can include one or more variants as compared to the sequence set forth in SEQ ID NO:3, SEQ ID NO:5, SEQ ID NO:6, SEQ ID NO:9, or SEQ ID NO:10. For example, the polypeptides provided herein can contain the entire amino acid sequence set forth in SEQ ID NO:3, SEQ ID NO:5, SEQ ID NO:6, SEQ ID NO:9, or SEQ ID NO:10, except that the amino acid sequence can contain from one to five (e.g., one to four, two to five, one to three, two to four, three to five, one to two, two to three, three to four, four to five, five, four, three, two, or one) amino acid additions, subtractions, and/or substitutions, or modifications. In some embodiments, for example, a polypeptide can contain the amino acid sequence set forth in SEQ ID NO:3 with one, two, three, four, or five single amino acid residue additions, subtractions, or substitutions. In some cases, a variant polypeptide can contain one or more additions, subtractions, and/or substitutions within the N-terminal portion of SEQ ID NO:2 (the first seven amino acids of SEQ ID NO:3). Examples of such polypeptides include, without limitation, polypeptides having an addition, deletion, or substitution of one or two amino acids within the SEQ ID NO:2 tag at the N- or C-terminus of SEQ ID NO:1 (e.g., a deletion of one or two of the glycine residues, substitution of threonine for one or both of the serine residues, or addition of one or two amino acid residues after the terminal cysteine). In some embodiments, the amino acid change(s) do not substantially reduce the ability of the sequence to bind to a therapeutic antibody.

Any amino acid residue set forth in the sequences provided herein can be subtracted, and any amino acid residue (e.g., any of the 20 conventional amino acid residues or any other type of amino acid, such as ornithine or citrulline) can be added to or substituted within the sequences set forth herein. The majority of naturally occurring amino acids are L-amino acids, and naturally occurring polypeptides are largely comprised of L-amino acids. D-amino acids are the enantiomers of L-amino acids. In some cases, a polypeptide as provided herein can contain one or more (e.g., one to three, two to four, three to six, five to eight, seven to ten, or more than ten) D-amino acids.

Polypeptides having one or more amino acid additions, subtractions, or substitutions relative to SEQ ID NO:3, SEQ ID NO:5, SEQ ID NO:6, SEQ ID NO:9, or SEQ ID NO:10 (also referred to herein as "variant" polypeptides) can be prepared and modified as described herein. Amino acid substitutions can be made, in some cases, by selecting substitutions that do not differ significantly in their effect on maintaining (a) the structure of the peptide backbone in the area of the substitution, (b) the charge or hydrophobicity of the molecule at the target site, or (c) the bulk of the side chain. For example, naturally occurring residues can be divided into groups based on side-chain properties: (1) hydrophobic amino acids (norleucine, methionine, alanine, valine, leucine, and isoleucine); (2) neutral hydrophilic amino acids (cysteine, serine, and threonine); (3) acidic amino acids (aspartic acid and glutamic acid); (4) basic amino acids (asparagine, glutamine, histidine, lysine, and arginine); (5) amino acids that influence chain orientation (glycine and proline); and (6) aromatic amino acids (tryptophan, tyrosine, and phenylalanine). Substitutions made within these groups can be considered conservative substitutions. Non-limiting examples of useful substitutions include, without limitation, substitution of valine for alanine, lysine for arginine, glutamine for asparagine, glutamic acid for aspartic acid, serine for cysteine, asparagine for glutamine, aspartic acid for glutamic acid, proline for glycine, arginine for histidine, leucine for isoleucine, isoleucine for leucine, arginine for lysine, leucine for methionine, leucine for phenylalanine, glycine for proline, threonine for serine, serine for threonine, tyrosine for tryptophan, phenylalanine for tyrosine, and/or leucine for valine. Substitutions between isosteric amino acid residues (e.g., glutamic acid and glutamine, or aspartic acid and asparagine) also may be considered to be conservative.

Further examples of conservative substitutions that can be made at any position within the polypeptides provided herein are set forth in TABLE 1.

TABLE 1

Examples of conservative amino acid substitutions

| Original Residue | Exemplary substitutions | Preferred substitutions |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn | Asn |
| Glu | Asp | Asp |
| Gly | Pro | Pro |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, Gln, Asn | Arg |
| Met | Leu, Phe, Ile | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleucine | Leu |

In some embodiments, a polypeptide can include one or more non-conservative substitutions. Non-conservative substitutions typically entail exchanging a member of one of the classes described above for a member of another class. Such production can be desirable to provide large quantities or alternative embodiments of the polypeptides and complexes provided herein. Whether an amino acid change results in a functional polypeptide can readily be determined by assaying the specific activity of the polypeptide variant (e.g., the ability of the variant to bind to an antibody) using, for example, the methods disclosed herein.

In some embodiments, a polypeptide as provided herein can have a length of, for example, 21 to 25, 22 to 26, or 23 to 27 amino acid residues (e.g., 21 to 24, 22 to 25, 23 to 26, 24 to 27, 21 to 23, 22 to 24, 23 to 25, 24 to 26, 25 to 27, 21 to 22, 22 to 23, 23 to 24, 24 to 25, 25 to 26, 26 to 27, 23, 24, 25, 26, or 27 amino acid residues).

In some embodiments, a polypeptide can have the amino acid sequence set forth in SEQ ID NO:3, SEQ ID NO:5, SEQ ID NO:6, SEQ ID NO:9, or SEQ ID NO:10, but with a particular number of amino acid substitutions. For example, a polypeptide can have the amino acid sequence of SEQ ID NO:3, SEQ ID NO:5, SEQ ID NO:6, SEQ ID NO:9, or SEQ ID NO:10, but with one, two, three, four, or five amino acid substitutions.

In some embodiments, a polypeptide as provided herein can include an amino acid sequence with at least 85% (e.g., at least 86%, at least 88%, at least 91%, at least 92%, at least 95%, at least 96%, or 100%) sequence identity to SEQ ID NO:3, SEQ ID NO:5, SEQ ID NO:6, SEQ ID NO:9, or SEQ ID NO:10. Percent sequence identity is calculated by determining the number of matched positions in aligned amino acid sequences, dividing the number of matched positions by the total number of aligned amino acids, and multiplying by 100. A matched position refers to a position in which identical amino acids occur at the same position in aligned amino acid sequences. Percent sequence identity also can be determined for any nucleic acid sequence.

The percent sequence identity between a particular nucleic acid or amino acid sequence and a sequence referenced by a particular sequence identification number is determined as follows. First, a nucleic acid or amino acid sequence is compared to the sequence set forth in a particular sequence identification number using the BLAST 2 Sequences (Bl2seq) program from the stand-alone version of BLASTZ containing BLASTN version 2.0.14 and BLASTP version 2.0.14. This stand-alone version of BLASTZ can be obtained online at fr.com/blast or at ncbi.nlm.nih.gov. Instructions explaining how to use the Bl2seq program can be found in the readme file accompanying BLASTZ. Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to -1; -r is set to 2; and all other options are left at their default setting. For example, the following command can be used to generate an output file containing a comparison between two sequences: C:\Bl2seq c:\seq1.txt -j c:\seq2.txt -p blastn -o c:\output.txt -q -1 -r 2. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence (e.g., SEQ ID NO:3), or by an articulated length (e.g., 20 consecutive nucleotides or amino acid residues from a sequence set forth in an identified sequence), followed by multiplying the resulting value by 100. For example, an amino acid sequence that has 24 matches when aligned with the sequence set forth in SEQ ID NO:3 is 96 percent identical to the sequence set forth in SEQ ID NO:3 (i.e., 24÷25×100=96.0). It is noted that the percent sequence identity value typically is rounded to the nearest tenth. For example, 75.11, 75.12, 75.13, and 75.14 is rounded down to 75.1, while 75.15, 75.16, 75.17, 75.18, and 75.19 is rounded up to 75.2. It also is noted that the length value will always be an integer.

Isolated polypeptides can be produced using any suitable method, including, without limitation, solid phase synthesis, and can be generated using manual techniques or automated techniques (e.g., using an Applied BioSystems (Foster City, Calif.) Peptide Synthesizer or a Biosearch Inc. (San Rafael, Calif.) automatic peptide synthesizer). The polypeptides provided herein also can be produced recombinantly or obtained commercially.

Variant polypeptides having conservative and/or non-conservative substitutions with respect to SEQ ID NO:3, SEQ ID NO:5, SEQ ID NO:6, SEQ ID NO:9, and SEQ ID NO:10 can be screened for binding to antibodies using any suitable assay. In some cases, for example, the binding activity of a polypeptide can be evaluated in vitro using surface plasmon resonance (e.g., using a Biacore X-100 Surface Plasmon Resonance device (GE Healthcare; Chicago, Ill.).

This document also provides nucleic acid molecules encoding the polypeptides provided herein. For example, this document provides nucleic acid molecules encoding the polypeptides of SEQ ID NO:3, SEQ ID NO:5, SEQ ID NO:6, SEQ ID NO:9, and SEQ ID NO:10, as well as nucleic acid molecules encoding polypeptides that are variants of the polypeptides having the amino acid sequences set forth in SEQ ID NO:3, SEQ ID NO:5, SEQ ID NO:6, SEQ ID NO:9, and SEQ ID NO:10. Thus, a nucleic acid molecule as provided herein can encode a polypeptide that contains the amino acid sequence set forth in SEQ ID NO:3, SEQ ID NO:5, SEQ ID NO:6, SEQ ID NO:9, or SEQ ID NO:10, except that the amino acid sequence contains one to five (e.g., one to four, two to five, one to three, two to four, one to two, three to four, five, four, three, two, or one) amino acid additions, subtractions, and substitutions as described herein.

The term "nucleic acid" as used herein encompasses both RNA and DNA, including cDNA, genomic DNA, and synthetic (e.g., chemically synthesized) DNA. The nucleic acid can be double-stranded or single-stranded. Where single-stranded, the nucleic acid can be the sense strand or the antisense strand. In addition, nucleic acid can be circular or linear.

The term "isolated," as used herein with reference to a nucleic acid, refers to a naturally-occurring nucleic acid that is not immediately contiguous with both of the sequences with which it is immediately contiguous (one on the 5' end and one on the 3' end) in the naturally-occurring genome of the organism from which it is derived. For example, an isolated nucleic acid can be, without limitation, a recombinant DNA molecule of any length, provided one of the nucleic acid sequences normally found immediately flanking that recombinant DNA molecule in a naturally-occurring genome is removed or absent. Thus, an isolated nucleic acid includes, without limitation, a recombinant DNA that exists as a separate molecule (e.g., a cDNA or a genomic DNA fragment produced by PCR or restriction endonuclease treatment) independent of other sequences, as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include a recombinant DNA molecule that is part of a hybrid or fusion nucleic acid sequence.

The term "isolated," as used herein with reference to a nucleic acid, also includes any non-naturally-occurring nucleic acid, since non-naturally-occurring nucleic acid sequences are not found in nature and do not have immediately contiguous sequences in a naturally-occurring genome. For example, non-naturally-occurring nucleic acid such as an engineered nucleic acid is considered to be isolated nucleic acid. Engineered nucleic acids can be generated using molecular cloning or chemical nucleic acid synthesis techniques. An isolated, non-naturally-occurring nucleic acid can be independent of other sequences, or incorporated into a vector, an autonomously replicating plasmid, a virus (e.g., a retrovirus, adenovirus, or herpes virus), or the genomic DNA of a prokaryote or eukaryote. In addition, a non-naturally-occurring nucleic acid can include a nucleic acid molecule that is part of a hybrid or fusion nucleic acid sequence.

It will be apparent to those of skill in the art that a nucleic acid existing among hundreds to millions of other nucleic acid molecules within, for example, cDNA or genomic libraries, or gel slices containing a genomic DNA restriction digest is not to be considered an isolated nucleic acid.

Isolated nucleic acid molecules can be produced using techniques including, without limitation, molecular cloning and chemical nucleic acid synthesis techniques. For example, polymerase chain reaction (PCR) techniques can be used to obtain an isolated nucleic acid containing a nucleotide sequence that encodes a polypeptide as provided herein. PCR refers to a procedure or technique in which target nucleic acids are enzymatically amplified. Sequence information from the ends of the region of interest or beyond typically is employed to design oligonucleotide primers that are identical in sequence to opposite strands of the template to be amplified. PCR can be used to amplify specific sequences from DNA as well as RNA, including sequences from total genomic DNA or total cellular RNA. Primers typically are 14 to 40 nucleotides in length, but can range from 10 nucleotides to hundreds of nucleotides in length. General PCR techniques are described, for example in *PCR Primer: A Laboratory Manual*, ed. by Dieffenbach and Dveksler, Cold Spring Harbor Laboratory Press, 1995. When using RNA as a source of template, reverse transcriptase can be used to synthesize complementary DNA (cDNA) strands. Ligase chain reaction, strand displacement amplification, self-sustained sequence replication, or nucleic acid sequence-based amplification also can be used to obtain isolated nucleic acids. See, for example, Lewis (1992) *Genetic Engineering News* 12:1; Guatelli et al. (1990) *Proc. Natl. Acad. Sci. USA* 87:1874-1878; and Weiss (1991) *Science* 254:1292.

Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector.

In some embodiments, the polypeptides provided herein can be labeled with a moiety that allows for detection. Without being bound by a particular mechanism, labeling of the amino- or carboxy-terminal tag portion of the polypeptide (e.g., at the N-terminal amine, or at an amino acid within the N- or C-terminal terminal tag sequence) can be particularly useful. Suitable labels include, for example, fluorescent moieties such as QD, fluorescein, sulforhodamine B, tetramethylrhodamine, phycoerythrin, and allophycocyanin; radionuclides such as $^{3}H$, $^{13}C$, $^{15}N$, $^{125}I$, and $^{99}Tcm$. Methods for attaching a detectable label to a polypeptide include those described in the Examples herein, for example. In some embodiments, a linker molecule (e.g., SMCC) can be thiol-coupled to one or more cysteine residues in the terminal extension sequence (e.g., SEQ ID NO:2), and also amine-coupled to a Quantum Dot or another label. Other covalent coupling methods (e.g., through a carboxyl or carbonyl) also can be used. In some cases, biotin can be added to the ε-amino group of a terminal lysine of a peptide during peptide synthesis. Streptavidin labeled QDs can be purchased as ready-made reagents; essentially, streptavidin is amine-coupled to a polyethylene glycol (PEG) coat on the QDs. Streptavidin and biotin have very high affinity for one another, so when a biotin-labeled peptide is combined with a streptavidin-labeled QD in solution, the two components can bind.

The polypeptides described herein can interact with various antibodies, including therapeutic monoclonal antibodies that bind to tumor antigens. Thus, this document also provides complexes that contain a polypeptide and an antibody. The polypeptide component of a complex can have the amino acid sequence of SEQ ID NO:3, SEQ ID NO:5, SEQ ID NO:6, SEQ ID NO:9, or SEQ ID NO:10, or the amino acid sequence of SEQ ID NO:3, SEQ ID NO:5, SEQ ID NO:6, SEQ ID NO:9, or SEQ ID NO:10 with one to five additions, subtractions, or substitutions. The polypeptide component also may be labeled. The antibody component of a complex can be a monoclonal antibody targeted to a tumor antigen. As described herein, useful antibodies can include, without limitation, bevacizumab, rituximab, trastuzumab, and atezolizumab. Methods for forming polypeptide-antibody complexes can include those known in the art, for example, such as the methods described in PCT Application No. PCT/US2017/045643, which is incorporated herein by reference in its entirety. In some cases, the labeled polypeptide and the antibody of interest can be combined at a particular ratio (e.g., a v:v ratio). For example, when the polypeptide is at a 10 mg/ml concentration, an antibody:polypeptide ratio of about 1:10, 1:15, 1:20, 1:25, or 1:30 may be particularly useful.

The polypeptides and/or polypeptide-antibody complexes described herein can be incorporated into compositions for use as research or clinical (e.g., diagnostic or therapeutic) tools. The compositions can include a polypeptide having the amino acid sequence of SEQ ID NO:3, SEQ ID NO:5, SEQ ID NO:6, SEQ ID NO:9, or SEQ ID NO:10, or the amino acid sequence of SEQ ID NO:3, SEQ ID NO:5, SEQ ID NO:6, SEQ ID NO:9, or SEQ ID NO:10 with one to five additions, subtractions, or substitutions, where the polypeptide is labeled as described herein, in combination with a carrier (e.g., water, saline, or a suitable buffer). In some cases, the compositions provided herein can include a polypeptide having the amino acid sequence of SEQ ID NO:3, SEQ ID NO:5, SEQ ID NO:6, SEQ ID NO:9, or SEQ ID NO:10, or the amino acid sequence of SEQ ID NO:3, SEQ ID NO:5, SEQ ID NO:6, SEQ ID NO:9, or SEQ ID NO:10 with one to five additions, subtractions, or substitutions, where the polypeptide is labeled as described herein and complexed with an antibody (e.g., a monoclonal therapeutic antibody), in combination with a carrier such as water, saline, or a suitable buffer, or another pharmaceutically acceptable carrier. Pharmaceutically acceptable carriers include, for example, pharmaceutically acceptable solvents, suspending agents, or any other pharmacologically inert vehicles for delivering antibodies to a subject.

Pharmaceutically acceptable carriers can be liquid or solid, and can be selected with the planned manner of administration in mind so as to provide for the desired bulk, consistency, and other pertinent transport and chemical properties, when combined with one or more labeled polypeptide-antibody complexes provided herein. In addition to water and saline, typical pharmaceutically acceptable carriers include, without limitation, binding agents (e.g., polyvinylpyrrolidone or hydroxypropyl methylcellulose), fillers (e.g., lactose or dextrose and other sugars, gelatin, or calcium sulfate), lubricants (e.g., starch, polyethylene glycol, or sodium acetate), disintegrates (e.g., starch or sodium starch glycolate), and wetting agents (e.g., sodium lauryl sulfate).

Pharmaceutical compositions containing complexes described herein can be administered by a number of methods, depending upon whether local or systemic treatment is desired. Administration can be, for example, parenteral (e.g., by subcutaneous, intrathecal, intraventricular, intramuscular, or intraperitoneal injection, or by intravenous drip), oral, topical (e.g., transdermal, sublingual, ophthalmic, or intranasal), or pulmonary (e.g., by inhalation or insufflation of powders or aerosols), or can occur by a combination of such methods. Administration can be rapid (e.g., by injection) or can occur over a period of time (e.g., by slow infusion or administration of slow release formulations).

The polypeptides, polypeptide-antibody complexes, and/or compositions described herein can be used as research and diagnostic tools. Thus, this document also provides methods for using the polypeptides described herein to, for example, identify antibodies to which the polypeptides can bind and form complexes. In addition, this document provides methods for using a labeled polypeptide-antibody complex as described herein to detect cells that express a particular antigen (e.g., a tumor marker such as, without limitation, VEGF, PD-L1, HER2, CD20, alphafetoprotein (AFP), carcinoembryonic antigen (CEA), CA-125, MUC-1, epithelial tumor antigen (ETA), melanoma-associated antigen (MAGE), tyrosinase, HER3, CD3, CD19, CD33, CD47, CD274, CD279, CD30, CD52, PD-1, CTLA4, GD2, BCR-ABL, NY-ESO-1, MAGE-1, MAGE-3, SSX2, Melan-A, EGFR, CD38, or RANK ligand). The methods can include, for example, contacting a cell (e.g., a tumor cell, either in vitro or in vivo) with a complex that includes a labeled polypeptide having the sequence of SEQ ID NO:3, SEQ ID NO:5, SEQ ID NO:6, SEQ ID NO:9, or SEQ ID NO:10, or a sequence that is at least 85% (e.g., 86%, 88%, 91%, 92%, 95%, or 96%) identical to the sequence of SEQ ID NO:3, SEQ ID NO:5, SEQ ID NO:6, SEQ ID NO:9, and SEQ ID NO:10, where the polypeptide is bound by an antibody that can bind selectively to the antigen. After incubation under conditions in which the antibody can interact with an antigen on the cell, if the antigen is present, the cells can be washed to remove unbound polypeptide-antibody complexes, and then evaluated to determine whether the presence of the label can be detected on the cell. In vitro methods may include detection by autoradiography, for example, or immunofluorescent immunohistochemistry. When conducted in vivo, the methods can include detecting labeled cells via PET scan or CT scan, for example, or via other suitable techniques for assessing cancer patients.

In some cases, a polypeptide-antibody complex (e.g., a polypeptide-QD-antibody complex) can be used as a companion tool to aid in diagnosis. For example, a melanoma metastasis in the brain might not express the antigen (e.g., PD-L1) expressed by the primary tumor, such that while the primary tumor might respond well to anti-PD-L1 immunotherapy, the brain tumor would not respond due to lack of the antigen. Thus, one or more labeled polypeptide-antibody complexes can be used to ascertain what marker(s) are expressed by the secondary tumor. Armed with such information, a clinician could treat primary and secondary lesions effectively, using a combination of therapeutic agents.

In some embodiments, the polypeptide-antibody complexes described herein can be used in therapeutic methods for treating subjects identified as having a clinical condition (e.g., cancer) associated with the antigen for the antibody within a given polypeptide-antibody complex. For example, a complex containing a radiolabeled polypeptide can be directed to a tumor by the antibody, providing targeted radioisotope delivery to the tumor.

Also provided herein are articles of manufacture containing one or more polypeptides, polypeptide-antibody complexes, or compositions as described herein. The components of an article of manufacture (e.g., the polypeptide(s) and the antibody(ies), or the polypeptide-antibody complex(es), and/or one or more buffers or diluents) can be provided separately or in combination, in one or more suitable containers. In some embodiments, the kit components (e.g., a combination of labeled polypeptide-antibody complexes) can be packaged as an in vitro diagnostic.

The invention will be further described in the following examples, which do not limit the scope of the invention described in the claims.

EXAMPLES

Example 1—Quantum Dot Labeling of Tumor Cells

A tagged polypeptide corresponding to amino acids 479 to 496 of HSA with a seven amino acid N-terminal sequence (CGSGGGSVVLNQLCVLHEKTPVSDR; SEQ ID NO:3) was linked to QD that emit at a wavelength of 605 nm. The QD had a PEG coating that prevented non-specific interaction and provided amino functional groups to allow further conjugation. A small molecule amine to sulfhydryl cross-linker, succinimidyl 4-(N-maleimidomethyl) cyclohexane-1-carboxylate (SMCC), was amine-coupled to the PEG-QD on one side, and then thiol-linked to the cysteine amino acid at the N-terminus of SEQ ID NO:3. All steps were done in darkness. SMCC was dissolved in dimethylsulfoxide (DMSO) to 10 mg/ml, and 66.8 µl SMCC was added to 250 µl QD (ThermoFisher) in 50 mM borate buffer pH 8.3. The mixture was allowed to stand for 1 hour, run over a PD-10 desalting column to remove unbound SMCC and peptide, and buffer swapped into 50 mM borate pH 7.2. The QD were thiol-coupled to 50 nmol of SEQ ID NO:3) in either 50 mM borate pH 7.2 with 10% DMSO, or in or straight DMSO, depending on the total volume of peptide and the final percent of DMSO in the solution. After a 9-hour incubation, the QD were precipitated out of solution, spun down, and resuspended in 2 ml of 100% DMSO.

Figure 2:
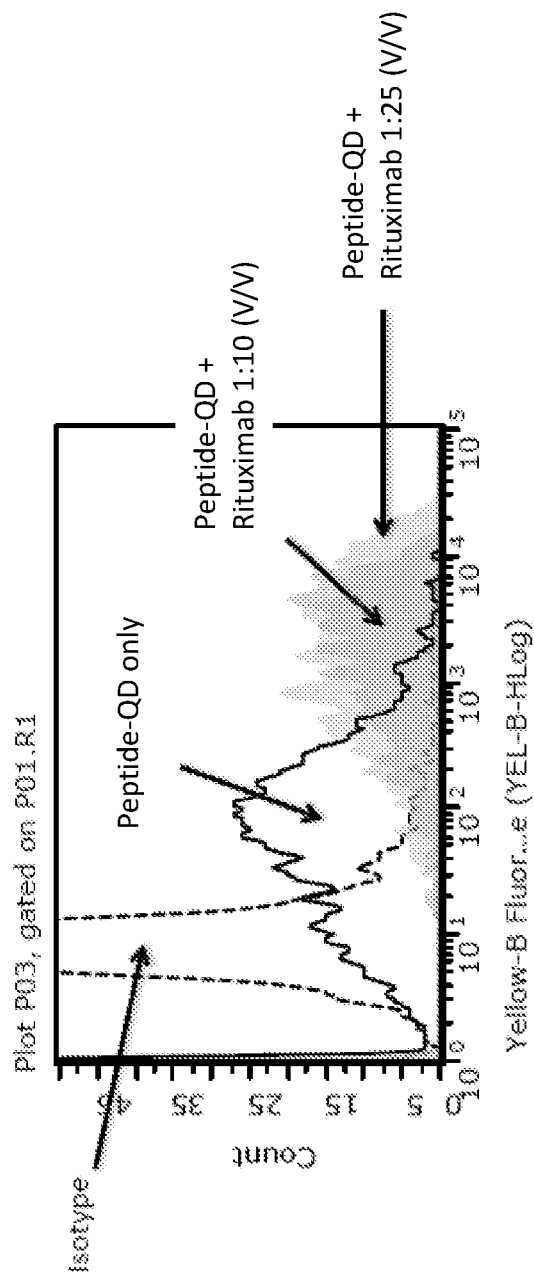
FIG. 2 is a histogram presentation of the data from FIG. 1.

The fluorescently labeled peptide was then bound to rituximab, trastuzumab, or atezolizumab and tested for binding to tumor cells expressing the pertinent tumor target. First, studies were conducted using the SEQ ID NO:3-QD-rituximab complex containing polypeptide:rituximab at ratios of 25:1 and 10:1 V/V (50 µl peptide+2 µl rituximab) for 1 hour, resulting in a complex that was stable until at least the next day. CD20+ Daudi lymphoma cells were incubated with isotype control, FITC-rituximab, polypeptide-QD only, polypeptide-QD-rituximab (10:1) complex, and polypeptide-QD-rituximab (25:1) complex for 30 minutes at 4° C. After washing with FACS buffer (PBS+0.5% BSA and 0.5% Na azide), the stained cells were analyzed by flow cytometry. The Daudi cells were 95% CD20+ (FIG. 1, top left), 11.62% positive when stained with polypeptide-QD only (FIG. 1, bottom left), and 57.02% and 61.31% positive with polypeptide-QD-rituximab at 10:1 and 25:1 (FIG. 1, bottom center and bottom right, respectively). A histogram representation of the data is shown in FIG. 2.

Figure 3:
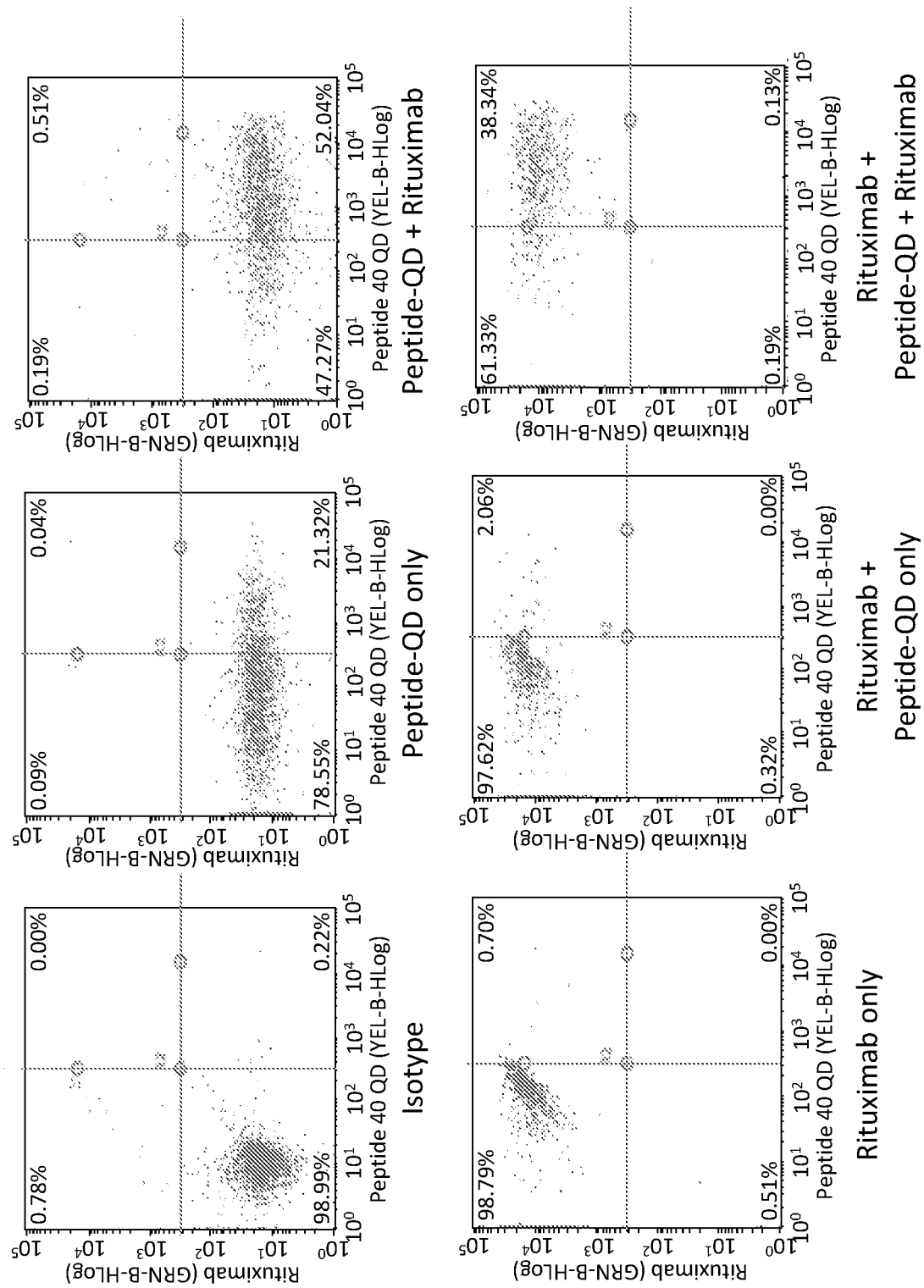
FIG. 3 is a series of scatter plots from flow cytometry studies using a SEQ ID NO:3-QD-rituximab complex as in FIG. 1, but in addition to the single stained samples, cells were stained with FITC-rituximab and SEQ ID NO:3-QD only (bottom center) or FITC-rituximab and SEQ ID NO:3-QD-rituximab polypeptide complex (bottom right).

Further studies were conducted as described above, but in addition to the single stained samples, cells were stained with FITC-rituximab and polypeptide-QD only (FIG. 3, bottom center) or FITC-rituximab and polypeptide-QD-rituximab complex (FIG. 3, bottom right).

Figure 4:
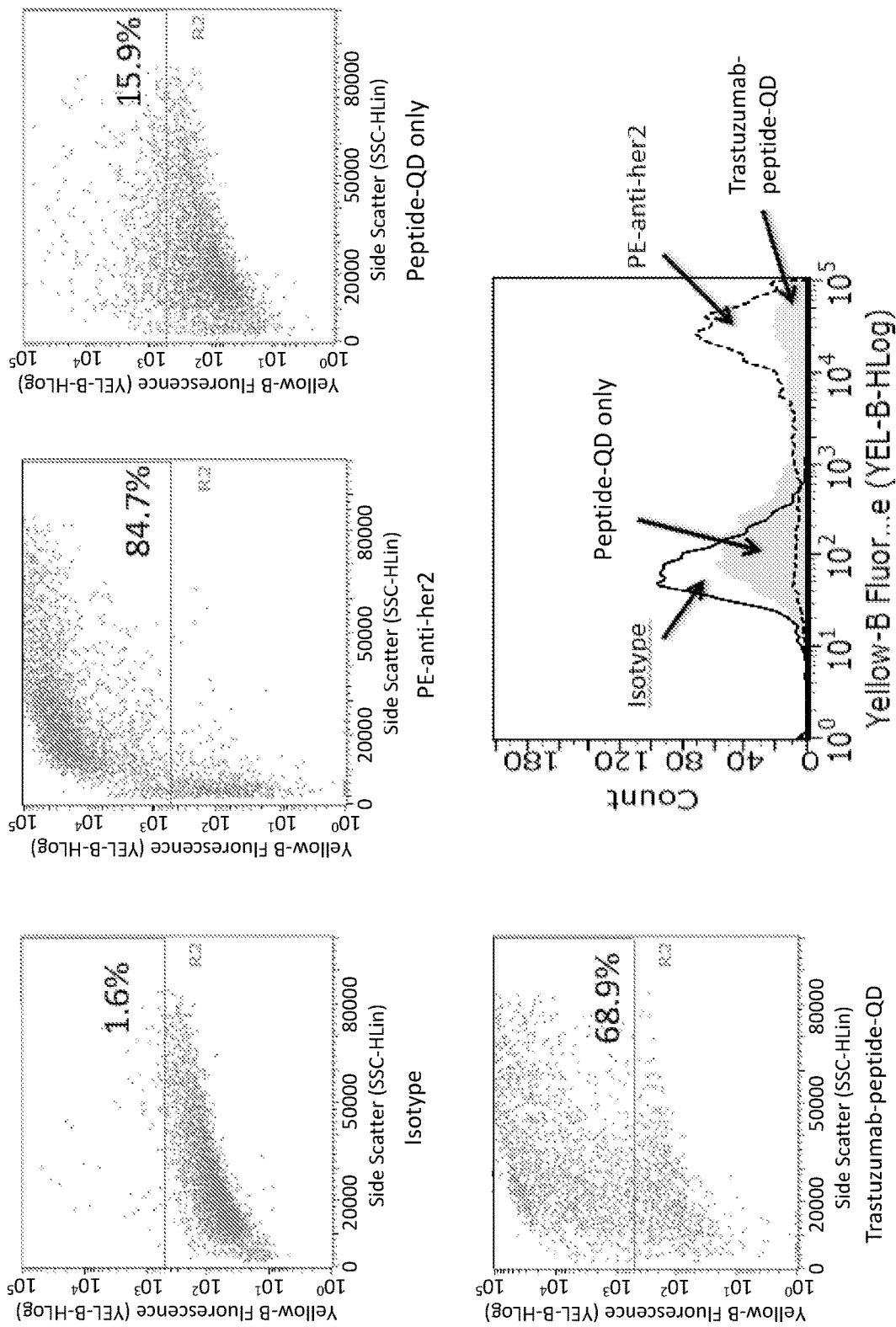
FIG. 4 is a series of scatter plots from flow cytometry studies using SK-Br-3 (HER2/neu-positive) cells stained with a SEQ ID NO:3-QD-trastuzumab complex. The SK-Br-3 cells were incubated with isotype control antibody (top left), PE-anti-HER2 (top middle), SEQ ID NO:3-QD only (top right), and SEQ ID NO:3-QD-trastuzumab complex (bottom left). The cells were 84.7% positive for HER2/neu, 15.9% positive with SEQ ID NO:3-QD only and 68.9% positive with SEQ ID NO:3-QD-trastuzumab complex. A histogram representation of the data is included at the bottom right of the figure.
Figure 5:
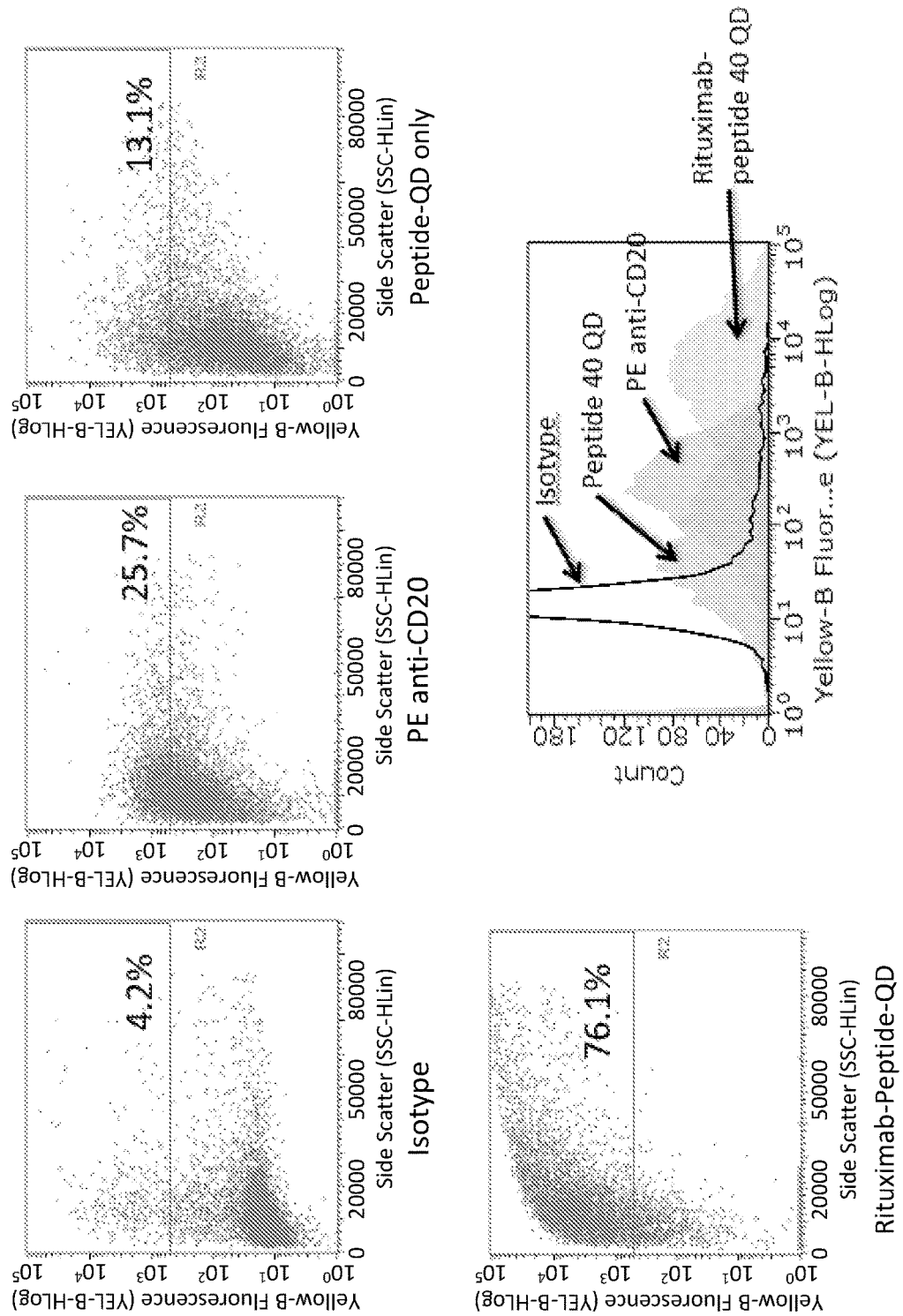
FIG. 5 is a series of scatter plots from flow cytometry studies as conducted in FIG. 1, but the Daudi cells were isolated from Daudi cell-derived mouse tumors rather than from tissue culture. The data were obtained using a tumor from a mouse that was not injected.

Additional experiments utilized HER2/neu-positive SK-Br-3 cells stained with polypeptide-QD bound to trastuzumab. The SK-Br-3 cells were incubated with isotype (FIG. 4, top left), PE-anti-HER2 (FIG. 4, top middle), polypeptide-QD only (FIG. 4, top right), and polypeptide-QD-trastuzumab complex (FIG. 4, bottom left). The cells were 84.7% positive for HER2/neu, 15.9% positive with polypeptide-QD only and 68.9% positive with the polypeptide-QD-trastuzumab complex. A histogram representation of the data is shown at the bottom right of FIG. 5.

Figure 6:
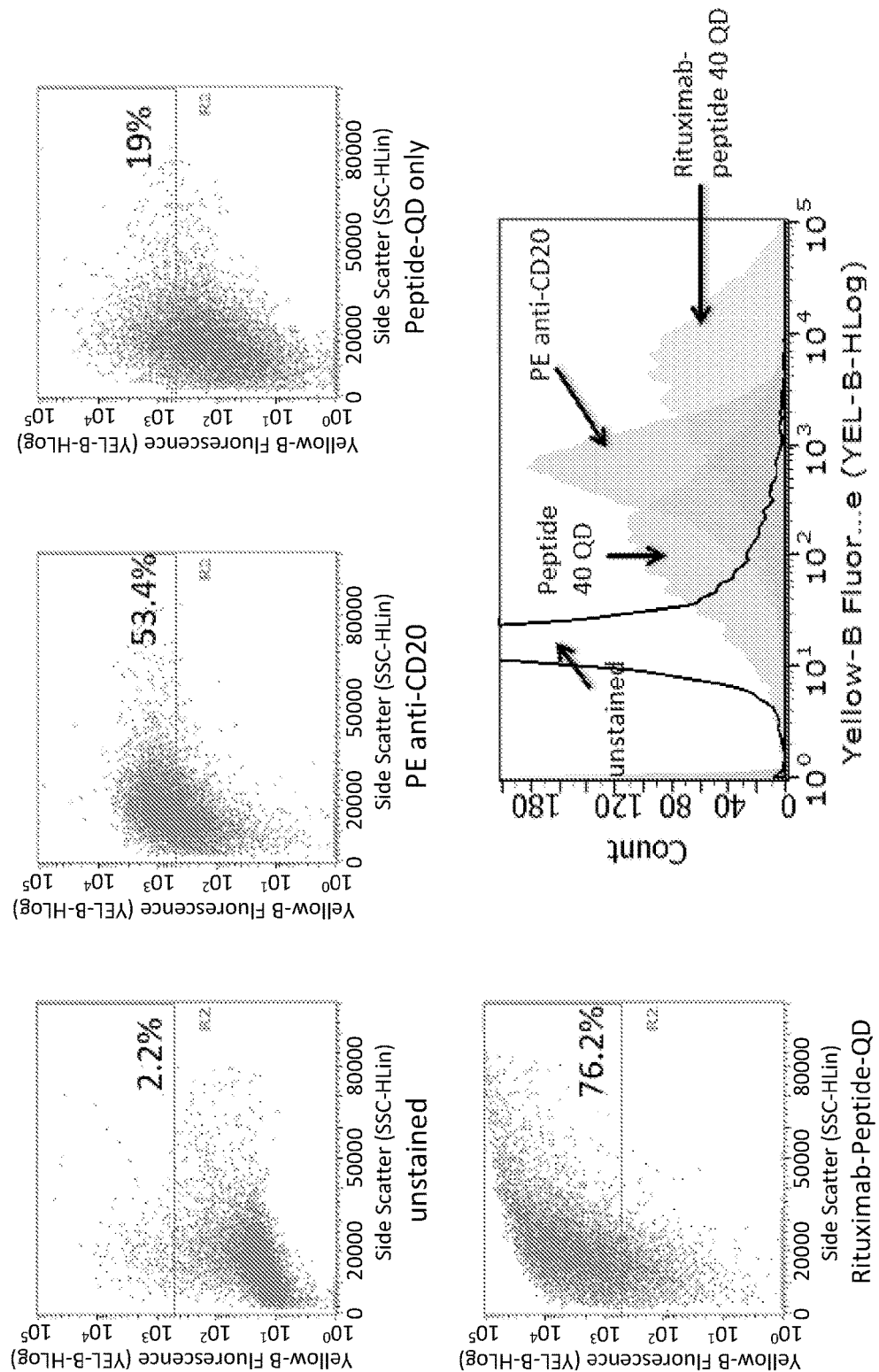
FIG. 6 is a series of scatter plots from flow cytometry studies as conducted in FIG. 1, but the Daudi cells were isolated from a Daudi cell-derived mouse tumor from a mouse that was injected intravenously with a SEQ ID NO:3-QD-rituximab complex to image the tumor ex vivo.

Studies also were conducted using Daudi cells isolated from a Daudi cell-derived mouse tumor, which were obtained from a mouse that was not (FIG. 5) or was (FIG. 6) injected intravenously with a polypeptide-QD-rituximab complex in an attempt to image the tumor in vivo. Histogram representations of the data also are included in FIGS. 5 and 6.

Figure 7:
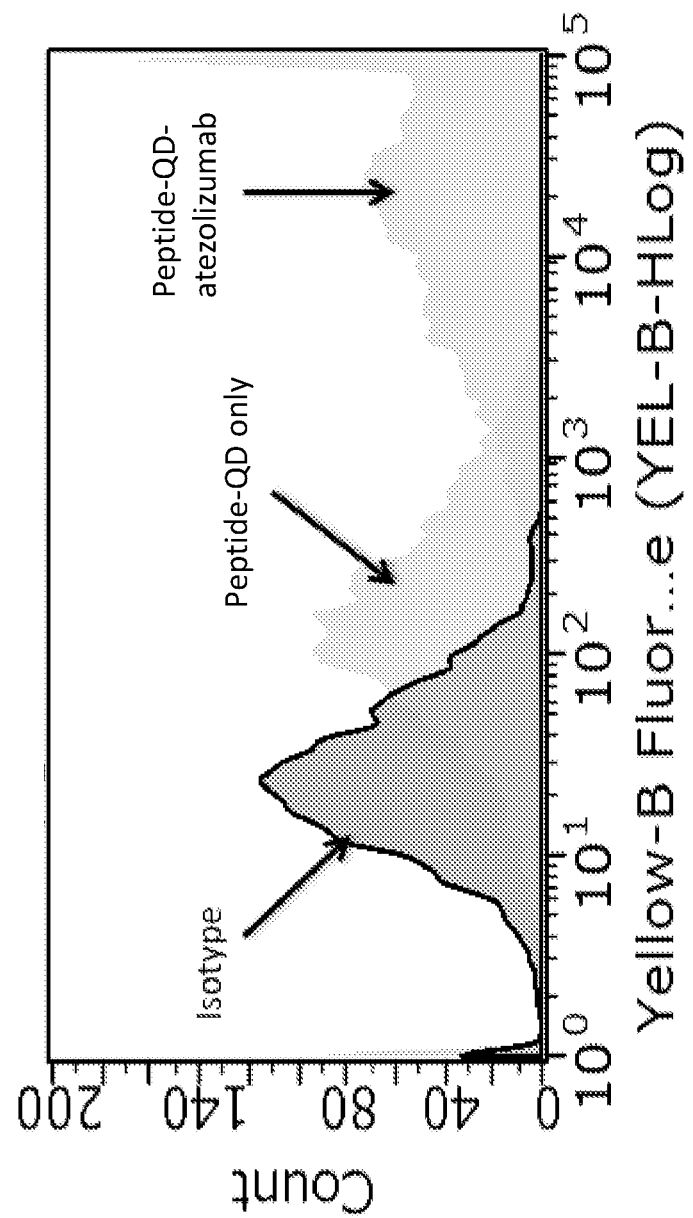
FIG. 7 is a histogram plotting staining of cells from a C8161 [programmed death-ligand 1+ (PD-L1+) melanoma] tumor that was removed from a nude mouse and incubated with isotype control, SEQ ID NO:3-QD only, and SEQ ID NO:3-QD-atezolizumab (anti-PD-L1) complex. Cells stained positively with the SEQ ID NO:3-QD-atezolizumab complex.

In addition, cells from a C8161 (PD-L1+ melanoma) tumor from a nude mouse were incubated with isotype control, polypeptide-QD only, and a polypeptide-QD-atezolizumab (anti-PD-L1) complex. The cells stained positively with the polypeptide-QD-atezolizumab complex (FIG. 7).

Thus, these studies demonstrated the utility of the labeled polypeptide-antibody complex with multiple tumor targets.

Example 2—Quantum Dot Labeling Via Biotin-Streptavidin

A peptide having a terminal lysine residue is coupled to biotin during synthesis, via the ε-amino group of the terminal lysine. Streptavidin labeled QDs are purchased as ready-made reagents (e.g., from ThermoFisher Scientific). The streptavidin-coupled QDs are combined with the biotin-coupled peptide, thus linking the QD to the peptide.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated polypeptide comprising the amino acid sequence set forth in SEQ ID NO:3, or comprising the amino acid sequence of SEQ ID NO:3 but with one or two amino acid deletions, additions, or substitutions within the N-terminal seven amino acids of SEQ ID NO:3.

2. The isolated polypeptide of claim 1, wherein the polypeptide comprises the amino acid sequence set forth in SEQ ID NO:3.

3. The isolated polypeptide of claim 1, wherein the polypeptide comprises the amino acid sequence of SEQ ID NO:3, but with one or two amino acid deletions, additions, or substitutions within the N-terminal seven amino acids of SEQ ID NO:3.

4. The isolated polypeptide of claim 1, wherein the polypeptide is labeled.

5. The isolated polypeptide of claim 4, wherein the polypeptide is labeled with a fluorescent moiety or a radionuclide.

6. The isolated polypeptide of claim 1, wherein the amino acid sequence of the polypeptide consists of the sequence set forth in SEQ ID NO:3.

7. A complex comprising:
a polypeptide that comprises the amino acid sequence set forth in SEQ ID NO:3, or comprising the amino acid sequence of SEQ ID NO:3 but with one or two amino acid deletions, additions, or substitutions within the N-terminal seven amino acids of SEQ ID NO:3, and
an antibody, wherein the antibody is selected from the group consisting of bevacizumab, rituximab, trastuzumab, alemtuzumab, atezolizumab, blinatumomab, brentuximab, cetuximab, denosumab, dinutuximab, ibritumomab, ipilimumab, nivolumab, obinutuzumab, ofatumumab, panitumumab, pembrolizumab, pertumumab, gemtuzumab, tositumomab, and muromonab.

8. The complex of claim 7, wherein the polypeptide comprises the amino acid sequence set forth in SEQ ID NO:3.

9. The complex of claim 7, wherein the polypeptide comprises the amino acid sequence of SEQ ID NO:3, but with one or two amino acid deletions, additions, or substitutions within the N-terminal seven amino acids of SEQ ID NO:3.

10. The complex of claim 7, wherein the polypeptide is labeled.

11. The complex of claim 10, wherein the polypeptide is labeled with a fluorescent moiety or a radionuclide.

12. The complex of claim 7, wherein the amino acid sequence of the polypeptide consists of the sequence set forth in SEQ ID NO:3.

13. A method for detecting a cell expressing on its surface a selected antigen, comprising:
contacting the cell with a complex that comprises (a) a detectably labeled polypeptide comprising the sequence set forth in SEQ ID NO:3, or comprising the sequence set forth in SEQ ID NO:3 but with one or two amino acid deletions, additions, or substitutions within the N-terminal seven amino acids of SEQ ID NO:3, and (b) an antibody that binds selectively to the antigen, wherein the contacting is under conditions in which the antibody can bind to the antigen, and wherein the antibody is selected from the group consisting of bevacizumab, rituximab, trastuzumab, alemtuzumab, atezolizumab, blinatumomab, brentuximab, cetuximab, denosumab, dinutuximab, ibritumomab, ipilimumab, nivolumab, obinutuzumab, ofatumumab, panitumumab, pembrolizumab, pertumumab, gemtuzumab, tositumomab, and muromonab; and detecting the presence of the label on the cell.

14. The method of claim 13, wherein the polypeptide comprises the amino acid sequence set forth in SEQ ID NO:3.

15. The method of claim 13, wherein the polypeptide comprises the amino acid sequence of SEQ ID NO:3, but with one or two amino acid deletions, additions, or substitutions within the N-terminal seven amino acids of SEQ ID NO:3.

16. The method of claim 13, wherein the polypeptide is labeled with a fluorescent moiety or a radionuclide.

17. The method of claim 13, further comprising washing the cell to remove unbound complexes.

* * * * *